United States Patent [19]

Caldini et al.

[11] 4,272,516

[45] Jun. 9, 1981

[54] PROCESS FOR IMPROVING TRANSCUTANEOUS AND TRANSFOLLICULAR ABSORPTION OF COSMETIC COMPOSITIONS

[75] Inventors: Oreste Caldini; Sandro Meucci, both of Florence, Italy

[73] Assignee: Societa Italo-Britannica-L. Manetti-H. Roberts Co., Florence, Italy

[21] Appl. No.: 43,819

[22] Filed: May 30, 1979

Related U.S. Application Data

[63] Continuation of Ser. No. 847,024, Oct. 31, 1977, abandoned.

[30] Foreign Application Priority Data

Nov. 8, 1976 [IT] Italy .............................. 52071 A/76

[51] Int. Cl.³ .............................................. A61K 7/06
[52] U.S. Cl. ...................................... 424/70; 424/59; 424/162; 424/168; 424/180; 424/195; 424/263; 424/343; 424/365
[58] Field of Search ................. 424/70, 343, 365, 263, 424/180, 162, 168, 195, 359

[56] References Cited

U.S. PATENT DOCUMENTS

| 3,630,654 | 12/1971 | Rosenthal et al. ................. 424/70 X |
| 3,663,716 | 5/1972 | Stolar ..................................... 424/343 |
| 3,697,644 | 10/1972 | Laiderman ............................. 424/70 |
| 3,899,578 | 8/1975 | Bird et al. ......................... 424/180 X |
| 3,949,072 | 4/1976 | Tenta ............................... 424/343 X |

OTHER PUBLICATIONS

Merck Index, 9th Ed., Merck & Co., Rahway, N.J., (1976), p. 148.
Kirk and Othmer, Encyclopedia of Chemical Technology, vol. 2, pp. 483-486, Interscience, New York, (1948).
Stekol, J. Biol. Chem., vol. 128, pp. 199-205, (1939).
Snapper et al., Biochem. Z., vol. 155, pp. 163-173, (1925).
Caldini et al., Boll. Chim Farm., vol. 114, pp. 545-553, (1975).

*Primary Examiner*—Dale R. Ore
*Attorney, Agent, or Firm*—Cushman, Darby & Cushman

[57] ABSTRACT

Benzyl alcohol is employed in an amount of 5.0 to 33.33% by weight of cosmetic composition as an absorption activator.

7 Claims, No Drawings

PROCESS FOR IMPROVING TRANSCUTANEOUS AND TRANSFOLLICULAR ABSORPTION OF COSMETIC COMPOSITIONS

This is a continuation of application Ser. No. 847,024 filed Oct. 31, 1977, now abandoned.

BACKGROUND OF THE INVENTION

The present invention refers to an activator for the absorption of cosmetic compositions, as well as to a series of new compositions for cosmetic use.

The activator, consisting of a specific component, that is, benzyl alcohol, has the function of facilitating the mechanism for the absorption of the other components through the skin and its associated organs.

Several chemical and physical properties and pharmacological activities of benzyl alcohol have been known for a long time, but it has never been thought to connect these with what may be one of its specific uses in cosmetics and dermopharmacy, as is now, however, the object of the present invention.

Benzyl alcohol, $C_7H_8O$, also called phenylcarbinol and α-hydroxytoluene, corresponds to the following chemical structure:

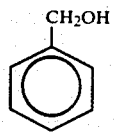

Its molecular weight, for this formula, is 108.13; the theoretical elementary analysis gives: C 77.75%, H 7.46%, O 14.80%. This is a natural constituent of the essential oils of jasmin, hyacinth, ylang-ylang and of balsams of Peru and Tolu, as well as storax. Commercially it is obtained by synthesis, starting from benzyl chloride, by reflux in the presence of sodium or potassium carbonate, in an anhydrous environment (R. E. Kirk and D. F. Othmer, Editors, Encyclopedia of Chemical Technology, Vol. 2, Interscience Encyclopedia, New York 1948, pp. 483-486). At ordinary temperatures and pressures it is a limpid, colourless, mobile and refracting liquid with a slight, aromatic, pleasing odour, of density (20° C.) 1.04535; melting point—15.19° C.; boiling point 204.7° C. (760 mm of Hg), 80.8° C. (5 mm of Hg). Soluble in about 25 parts of water and in 1.5 parts of 1:1 water—ethanol; miscible with ethanol, ethyl ether, chloroform and many other polar or apolar organic solvents (The Merck Index, Ninth Ed., No. 1138, p. 148, Rahway, N.J., 1976). It is used in the manufacture of perfumes, pharmaceutical and parapharmaceutical products and its esters are used in soaps, in perfumes and in food flavourings (A. K. Doolittle, The Technology of Solvents and Plasticizers, Wiley, N.Y. 1954, p. 672; I. Mellan, Industrial Solvents, Reinhold, N.Y. 1950, p. 86, p. 519).

Its local antiseptic and anaesthetic properties are currently used, and this use is favoured by the fact that its acute toxicity is very low ($LD_{50} = 3100$ mg/kg, oral, rat), while toxic effects in subacute or chronic measure have not been recorded, above all because of the fact that it is rapidly oxidised within the organism and eliminated in the form of hippuric acid or benzoyl glycine (H. F. Smyth, Jr., C. P. Carpenter and C. S. Weil, Arch.Ind.Hyg. Occupational Med., 4, 119; 1951). Within 6 hours of the oral ingestion of 1.5 g of benzyl alcohol human subjects eliminate 75–85% of the dose in the urine as hippuric acid (I. Snapper, A. Grunbaum and S. Sturkop, Biochem.Z., 155, 163; 1925; see also: J. A. Stekol, J.Biol. Chem., 128, 199; 1939).

SUMMARY OF THE INVENTION

The present invention takes advantage, however, of unforeseen characteristics due to which benzyl alcohol, the structure of which is the simplest possible in which an aromatic nucleus (lipophile) and an hydroxymethyl group (hydrophile) co-exist, may serve as the ideal vehicle to favour the transcutaneous and transfollicular absorption of substances particularly active and useful in the field of cosmetics and dermopharmacy.

As is well known, the study of the mechanisms of absorption through organized cellular barriers has assumed a particular importance in cosmetology and in dermopharmacy in recent times. In each biological membrane concerned with exchange with the environment, one or more layers of polymeric molecules of lipid nature are present, with polar extremities oriented in a uniform manner. In the particular case which forms the subject of the present invention, it follows that the protective function exercised by the cutaneous covering is permitted, by inter alia its restricted permeability to most of the extraneous substances with which it may come into contact, in as much as these are either insufficiently hydrophilic or insufficiently lipophilic. The part of the skin which contributes more than any other to this defence is represented, as is readily understood, by the horny layer.

If the chemical and physical parameters which regulate the action of the motive forces responsible for the cutaneous absorption are examined, one sees that the diffusion process may be embodied as a passive transport scheme, being determined mainly by the limit of diffusibility and by the extremely complex fine structure of the intercellular keratin.

Nevertheless, even if the skin functions in this way as a sufficiently effective barrier against penetration of different substances, it was a serious error to have considered it at one time as only an inert shield. It represents on the other hand a morphological and structural unity which exhibits specific affinities for different substances with which it comes into contact, and the skin, even through the associated organs which are concerned primarily with excretive functions, can therefore, behave as an organ which is variously selective with regard to absorbtion.

One can therefore consider a direct mechanism for the cutaneous absorption of various substances, when the latter are of a lipoid nature and have relatively simple structures; in such a case they dissolve in the covering, and transepidermal absorption takes place. If, on the other hand, the passage of extraneous substances takes place through the cutaneously associated organs by an indirect mechanism, transglandular and transfollicular absorption takes place.

In the second case many physical and chemical factors come into play because the absorption takes place through organs which are very different from one another, such as piliferous follicles, sebaceous glands and sudoriparous glands. Among the various factors, it is necessary to record the maximum or minimum surface activity of the compound or compounds applied, their degree of moisture, the temperature of application, their emulsifying ability, the energy with which the rubbing or massaging is carried out during the application, and so on.

One chemical and physical explanation which is accepted as defining the phenomena of permeability on the basis of transport mechanisms through biomembranes, imposes a consideration of the skin as a bioactive membrane, all the transport phenomena which take place in it being considered not according to the criteria of equilibria studied by classical thermodynamics, but according to those of non-equilibria on which the thermodynamics of irreversible processes are based (O. Caldini, M. Mannelli and C. Pisaturo), *Boll. Chim Farm.* 114, 545–553; 1975; see also C. Botre, "Thermodynamics of irreversible processes," ed. Bulzoni, Roma 1971, passim).

The data of solubility and permeability lead us to consider that non-polar solutes, as much as polar solutes, diffuse through the horny layer by different molecular mechanisms of permeation. In fact the water-soluble molecules and the liposoluble ones are characterised by very different values of free energy of activation, diffusion and activation for diffusion. The coefficients of distribution in membranes for water-soluble compounds are nearly all near to unity and thus indicate that they dissolve in hydrated regions, for example in kerational zones. The ingress of water-molecules or of other highly polar molecules should then be explained as a tendency to diffuse within these aqueous regions, probably localized near the external surfaces of fibres, or in those parts of the corneal layer characterised by intracellular keratin, rather than deep within the semicrystalline parts. On the contrary, lipid molecules and other non-polar molecules should dissolve and diffuse in the lipid zone comprising the fibres of the eukeratinal fine structure.

It has now been discovered that the benzyl alcohol molecule is such that it can take advantage of both means of passage thus acting as an ideal vehicle, which accordingly forms the subject of the present invention.

Most of the preparations for cutaneous application are based on the use of compounds of a non-polar nature. These are then conveyed into the aqueous phase by means of surface-active agents of various types, thus giving rise to emulsions or particulate suspensions. If the nature of the vehicular substances and the degree to which they can retain the active principles are not considered, it is observed that the determining factor for the taking up and diffusion of the various molecules in the tissue is given by the endogenous hydration at the level of the corneal layer; and what is more, it is just this diffusion which basically determines the speed of the process in its entirety. If, therefore, there are added to the water molecules, which thus exercise the basic function in such processes, molecules, structurally not much more complex, of benzyl alcohol, in which an aromatic lipophilic component is present, the mobility of the entire active unit applied to the skin is increased surprisingly thereby. In fact, when a particular compound is sufficiently liposoluble, the aqueous regions of the keratin are not necessarily involved in the dissolving process, and the passage can even take place according to the coefficient of distribution between the water and horny layer; roughly the same relationships also apply in the case of the transglandular and transfollicular passage.

It was not foreseeable however that such theoretical considerations would be confirmed by practical experience. In fact, surprisingly, it has been found that benzyl alcohol is a substance which, because of the extreme simplicity of its molecular structure, both in its aromatic half (lipophilic) and in its aliphatic part (hydrophilic), acts as an ideal vehicle for favouring the transcutaneous, transfollicular and transglandular absorption of active components in formulations of cosmetic and dermopharmaceutical products. Benzyl alcohol, because of its function as a lipo-hydrophilic vehicle, is readily introduced into such dermopharmaceutical and cosmetic formulations, in concentrations between a minimum of 5% and a maximum of 33.3%.

In the preparation of dermopharmaceutical and cosmetic compositions containing benzyl alcohol as an activator for cutaneous absorption, its distribution, in the case of emulsions, takes place equally well in the continuous or the disperse phase, independently of the nature of one or the other, that is, independently of whether the emulsion is of the oil-in-water type or the water-in-oil type. In the case of single-phase formulations (lotions, jellies, alcoholates, ointments etc.) the solubility of benzyl alcohol is such that the system is homogeneous within the limits of concentration mentioned above.

In any case it must be remembered that the benzyl alcohol favours the absorption mechanisms mentioned above, both in the sense of the lipophilic manner and in the hydrophilic manner, because of its elementary lipohydrophilic structure (HLB=5.74).

An object of the present invention is, therefore, an absorption activator for cosmetic compositions, consisting of benzyl alcohol, employed in a quantity of between 5.00 and 33.3% by weight of the said benzyl alcohol with respect to the total weight of the composition.

A further object of this invention is a cosmetic composition containing benzyl alcohol as an absorption activator in a quantity of between 5.00 and 33.3% by weight of the said benzyl alcohol with respect to the total weight of the composition.

Cosmetic compositions according to this invention may be: a lotion for reactivating the hair, a reactivating jelly, a tonic milk, a reactivating cream, a cleansing lotion, an antihyperkeratosis cream, an antigrease cream.

In the following examples, purely and simply for the purpose of illustration, and without restricting the scope of this invention in any way, it is possible to give a few dermopharmaceutical and cosmetic formulations in which benzyl alcohol is employed in concentrations of between 5.00 and 33.33% by weight, alongside other known and variably active components, for the aforesaid purposes. The chosen range for the absorption action which forms the subject of the present invention is explained by what has been said at the beginning, that is to say, that other characteristics and other activities were known for benzyl alcohol: for example, below a concentration of 5.00% an antimicrobic action is manifested, while for local-anaesthetising and anti-pruroginic action one resorts to concentrations not lower than 33.33%. The concentrations lying within the chosen range for the field of application of the present invention have been found to be the most suitable, however, for favouring the transcutaneous absorption processes of the active principles of dermopharmaceutical and cosmetological interest, in particularly stable and balanced formulations. In the following examples the percentages are by weight.

DESCRIPTION OF THE PREFERRED EMBODIMENTS

| "Reactivating Lotion for the Hair" | |
|---|---|
| Benzyl alcohol | 12% |
| Nicotinyl alcohol | 0.5% |
| Resorcinol | 0.5% |
| Propylene glycol | 4.0% |
| Polyoxyethylene sorbitan monooleate (Polysorbate 80) | 1.0% |
| Polyethylene glycol 600 | 2.0% |
| Perfume | 1.0% |
| Ethyl alcohol 95% (V/V) | 47.5% |
| De-ionised water | 31.5% |

By comparison with the same formula in which the benzyl alcohol is replaced by proportional parts of water and of ethyl alcohol, it is possible to establish, in groups of 5-7 subjects in normal conditions, that after a standard treatment for four weeks (application of the lotion after the morning toilet; neutral shampoo once per week), the count of hairs remaining on the comb was reduced by on average 45-55% with respect to the values established before the treatment, and 40-45% with respect to values obtainable following the treatment without benzyl alcohol (stimulating action of nicotinyl alcohol and resorcinol).

| Reactivating Jelly | | |
|---|---|---|
| (A) | Benzyl alcohol | 4.0% |
| | Diethanolamine | 0.7% |
| | Ethyl alcohol 95% (V/V) | 11.6% |
| | Richter Collagen | 5.0% |
| | Perfume | 0.1% |
| | De-ionised water | 11.6% |
| (B) | Carboxypolymethylene (Carbopol 940) | 1.0% |
| | De-ionised water | 60.0% |
| | Propylene glycol | 6.0% |

A and B are blended together slowly. By comparison with the same formula in which the benzyl alcohol is replaced by proportional parts of water and ethyl alcohol, it is possible to observe that the aesthetic conditions of the skin (hands, neck, face) in groups of 4-5 female subjects, aged from 35 to 46 years, are notably improved with the constant use of the formula in which benzyl alcohol is present. The increase in the cutaneous reflection, measured with a light meter and a photoelectric cell on the back of the hand, was on average between 37-46% with respect to the values established before the treatment, and 31-38% with respect to the values obtainable following the treatment without benzyl alcohol (hydrating action of the collagen and of the propylene glycol).

EXAMPLE III

| Tonic Milk | | |
|---|---|---|
| (A) | Benzyl alcohol | 5.0% |
| | Self-emulsifying glyceryl monostearate | 1.5% |
| | Polyoxyethylene lauryl ether (Brij 35 Atlas) | 1.2% |
| | Propylene glycol | 2.0% |
| | Isopropyl myristate | 7.0% |
| | Cetyl-stearyl alcohol | 0.75% |
| (B) | Carboxypolymethylene (Carbopol 934) | 0.3% |
| | Sodium carboxymethylcellulose | 0.5% |
| | Hydrating mucopolysaccharides | 3.0% |
| | Extract of Hamamelis Virginiana leaves | 2.0% |
| | Benzyl alcohol | 5.0% |
| | Methyl p-hydroxybenzoate | 0.15% |

| Tonic Milk -continued | | |
|---|---|---|
| | Propyl p-hydroxybenzoate | 0.05% |
| | De-ionised water | 70.52% |
| (C) | Triethanolamine | 0.23% |
| | Perfume | 0.80% |

A is poured into B, under agitation, at 75° C., and C, followed by the perfume, is added to the emulsion at 40° C. The comparison with the same formula in which the benzyl alcohol is replaced by proportional parts of water and of ethyl alcohol was carried out in Example II and provided similar results, with the percentage increase in the cutaneous reflection (in the zigomatic periobitary region) of the same order of magnitude (activation by the hydrating action of the mucipolysaccharides and of propylene glycol).

EXAMPLE IV

| Reactivating Cream | | |
|---|---|---|
| (A) | Benzyl alcohol | 2.00% |
| | Self-emulsifying glyceryl monostearate | 13.00% |
| | Cetyl-stearyl alcohol | 1.00% |
| | Isopropyl myristate | 8.00% |
| | Propylene glycol | 2.00% |
| (B) | Glycerine | 8.00% |
| | Benzyl alcohol | 6.50% |
| | Lettuce extract | 2.00% |
| | Richter Collagen | 5.00% |
| | Sodium Stearate | 0.10% |
| | Methyl p-hyrdoxybenzoate | 0.15% |
| | Propyl p-hydroxybenzoate | 0.05% |
| | De-ionised water | 51.20% |
| (C) | Perfume | 1.00% |

A is poured into B, under agitation, at 70° C., and C is added to the emulsion, at 40° C. The comparison with the same formula in which benzyl alcohol was replaced by equal parts of water was carried out as in Example II and produced analogous results, with percentage increases in the cutaneous reflection (antero-lateral region of the neck) of the same order of magnitude (activation by the hydrating action of the vegetable extract, collagen, propylene glycol and of glycerine).

EXAMPLE V

| Cleansing Lotion | |
|---|---|
| Benzyl alcohol | 33.33% |
| Glycerine | 2.00% |
| Propylene glycol | 5.00% |
| Thymol | 0.40% |
| Polyethylene glycol 600 | 3.00% |
| Ethyl alcohol 95% (V/V) | 33.33% |
| De-ionised water | 22.94% |

By comparison with the same formula in which the benzyl alcohol was replaced by proportional parts of water and ethyl alcohol, it was possible to observe that the aesthetic condition of the cutaneous area subjected to treatment (cheeks, nose, throat, neck etc.) in groups of 4-5 female subjects aged between 18 and 34 years, was effectively improved by the constant use of the formula in which benzyl alcohol was present. The count of the blackheads was reduced by 40-44% with respect to the values established before the treatment, and by 36-39% with respect to the values obtainable following treatment without the benzyl alcohol (purifying action of the thymol and of the glycols).

EXAMPLE VI

| Antihyperkeratosis Cream | | |
| --- | --- | --- |
| (A) | Benzyl alcohol | 3.00% |
| | Self-emulsifying glyceryl monostearate | 13.00% |
| | Isopropyl myristate | 8.00% |
| | Propylene glycol | 2.00% |
| (B) | C. L. Richter biosulphur liquid (solubilized sulfur) | 0.20% |
| | Benzyl alcohol | 8.00% |
| | Allantoin | 0.50% |
| | Sodium stearate | 0.10% |
| | Anhydrous sodium acetate | 0.20% |
| | De-ionised water | 64.40% |
| (C) | Perfume | 0.60% |

A is poured into B, under agitation, at 70° C., and C is added to the emulsion at 40° C. By comparison with the same formula in which the benzyl alcohol was replaced by proportional parts of isopropyl myristate and of water, it was possible to observe that the aesthetic conditions of a hyperkeratosic skin (hands, neck, face, lower limbs etc.) in groups of 4–5 female subjects, aged between 34 and 46 years, was effectively improved by the constant use of the formula in which benzyl alcohol was present. In the absence of a method suitable for ensuring the objectiveness of the results, a favourability test according to the double blind technique was carried out using the formula without the benzyl alcohol as a placebo. In each case the response in favour of the formula with benzyl alcohol exceeded significantly values of between 65 and 80%.

EXAMPLE VII

| Antigrease Cream | | |
| --- | --- | --- |
| (A) | Benzyl alcohol | 12.50% |
| | Liquid paraffin | 5.00% |
| | Apicerol (Lanolin and Beeswax) | 6.00% |
| | Ethoxylated lanolin | 4.00% |
| | Oleyl alcohol (Eutanol Henkel) | 2.00% |
| (B) | Crystalline sorbitol | 3.00% |
| | Benzyl alcohol | 6.50% |
| | Liquid extract of ivy | 1.00% |
| | Liquid extract of birch | 1.00% |
| | Liquid extract of horse chestnut | 0.25% |
| | Escin | 0.30% |
| | Anhydrous sodium acetate | 0.20% |
| | De-ionised water | 57.65% |
| (C) | Perfume | 0.60% |

A is poured into B, under agitation, at 70° C., and C is added to the emulsion at 40° C. By comparison with the same formula in which the benzyl alcohol was replaced by proportional parts of oleyl alcohol and of water, a significant flattening of the kymographic traces indicating the nodular relief of the skin (thighs, buttocks) was found along pre-established lines. In particular, the comparison with the data taken before treatment, in groups of female subjects aged between 34 and 49 years, was considered using the other thigh or the other buttock of the same subject treated with the formulation devoid of benzyl alcohol as the control. The treatment consisted of massaging the nodular area, affected by mesenchyma (generally and improperly called "cellulite"), for 5 minutes, twice a day at a fixed time, with ten grams of one or the other formula, the kymographic relief being carried out after 10-15-20 days of treatment. The flattening of the trace with the use of the formula containing benzyl alcohol was, on average about 65–76%; with the use of the formula not containing benzyl alcohol this was on average, 36–45% (vascularizing and restoring action of the vegetable extract and of the escin).

It is clear that in every formula of the examples recorded above, and in any other which may be given as non-limitative examples, qualitative and quantitative variations in the compositions, as far as possible, fall within the field of the present invention, since the general phenomenon on which it is based, as well as the particular field in which it is usefully employed, is clear.

It is, therefore, understood that the invention is not limited to the embodiments described above, but that all the variations of execution and of use which will be seen as obvious to the experts in this art fall within its scope.

We claim:

1. A process of improving the transcutaneous and transfollicular absorption of a hair lotion having the following composition in parts by weight,
Nicotinyl alcohol: 0.5
Resorcinol: 0.5
Propylene glycol: 4.0
Polysorbate 80: 1.0
Polyethylene glycol 600: 2.0
Perfume: 1.0
Ethyl alcohol 95%: 47.5
De-ionised water: 31.5
comprising the steps of
(a) adding to said hair lotion 12.0 parts by weight of benzyl alcohol as an absorption activator, to form an improved hair lotion, and
(b) applying an effective amount of said improved hair lotion to the hair.

2. A process of improving the transcutaneous and transfollicular absorption of a jelly having the following composition in parts by weight,
Diethanolamine: 0.7
Ethyl alcohol 95%: 11.6
Collagen: 5.0
Perfume: 0.1
De-ionised water: 71.6
Carbopol 934: 1.0
Propylene glycol: 6.0
comprising the steps of
(a) adding to said jelly 4.0 parts by weight of benzyl alcohol as an absorption activator to form an improved jelly, and
(b) applying an effective amount of said improved jelly to the body.

3. A process for improving the transcutaneous and transfollicular absorption of a tonic milk having the following composition in parts by weight,
self-emulsifying Glyceryl monostearate: 1.50
Polyoxyethylene lauryl ether: 1.20
Propylene glycol: 2.00
Isopropyl myristate: 7.00
Cetyl-stearyl alcohol: 0.75
Carbopol 934: 0.30
Carboxymethylcellulose: 0.50
Hydrating mucopolysaccharides: 3.00
Extract of Hammelis leaves: 2.00
Methyl p-hydroxybenzoate: 0.15
Perfume: 0.80
De-ionised water: 70.52
Triethanolamine: 0.23
comprising the steps of (a) adding to said tonic milk 10.0 parts by weight of benzyl alcohol as an absorption to form an improved tonic milk, and
(b) applying an effective amount of said improved tonic milk to the body.

4. A process for improving the transcutaneous and transfollicular absorption of a cream having the following composition in parts by weight,
Self-emulsifying glyceryl monosterate: 13.00
Cetyl-stearyl alcohol: 1.00
isopropyl myristate: 8.00
Propylene glycol: 2.00
Glycerine: 8.00
Lettuce extract: 2.00
Collagen: 5.00
Sodium stearate: 0.10
methyl p-hydroxybenzoate: 0.15
Propyl p-hydroxybenzoate: 0.05
Perfume: 1.00
De-ionised water: 51.20
comprising the steps of
(a) adding 8.5 parts by weight of benzyl alcohol as an absorption activator to form an improved cream, and
(b) applying an effective amount of said improved cream to the body.

5. A process for improving the transcutaneous and transfollicular absorption of a detergent lotion having the following composition in parts by weight,
Glycerine: 2.00
Propylene glycol: 5.00
Thymol: 0.40
Polyethylene glycol 600: 3.00
Ethyl Alcohol 95%: 33.33
De-ionised water: 22.94
comprising the steps of
(a) adding to said detergent lotion 33.33 parts by weight of benzyl alcohol as an absorption activator to form an improved detergent lotion, and
(b) applying an effective amount of said improved detergent lotion to the body.

6. A process of improving the transcutaneous and transfollicular absorption of an antihyperkertosis cream having the following composition in parts by weight,
Self-emulsifying glyceryl monostearate: 13.00
Isopropyl myristate: 8.00
Propylene glycol: 2.00
Solubilized sulphur: 0.20
Allantoin: 0.50
Sodium stearate: 0.10
Perfume: 0.60
Anhydrous sodium acetate: 0.20
De-ionised water: 64.40
comprising steps of
(a) adding to said antihyperkeratosis cream 11.0 parts by weight of benzyl alcohol as an absorption activator to form an improved antihyperkeratosis cream, and
(b) applying an effective amount of said improved antihyperkeratosis cream to the body.

7. A process of improving the transcutaneous and transfollicular absorption of an antigrease cream having the following composition in parts by weight,
Liquid paraffin: 5.00
Apicerol (Lanolin and Beeswax): 6.00
Etoxylated lanolin: 4.00
Oleyl alcohol (Eutanol): 2.00
Crystalline sorbitol: 3.00
Liquid extract of ivy: 1.00
Liquid extract of horse chestnut: 0.25
Escin: 0.30
Sodium dehydroacetate: 0.20
Perfume: 0.60
De-ionised water: 57.65
Liquid extract of birch: 1.00
comprising the steps of
(a) adding to said antigrease cream 19.00 parts by weight of benzyl alcohol as an absorption activator to form an improved antigrease cream, and
(b) applying an effective amount of said improved antigrease cream to the body.

* * * * *